US008961458B2

United States Patent
Pesach et al.

(10) Patent No.: US 8,961,458 B2
(45) Date of Patent: Feb. 24, 2015

(54) DEVICE AND METHOD FOR DRUG DELIVERY

(75) Inventors: Benny Pesach, Rosh-ha ayin (IL); Gabriel Bitton, Jerusalem (IL); Ron Nagar, Tel Aviv (IL); Ram Weiss, Haifa (IL)

(73) Assignee: Insuline Medical Ltd., Petach-Tikva (IL)

( * ) Notice: Subject to any disclaimer, the term of this patent is extended or adjusted under 35 U.S.C. 154(b) by 961 days.

(21) Appl. No.: 13/127,823

(22) PCT Filed: Nov. 6, 2009

(86) PCT No.: PCT/IB2009/007600
§ 371 (c)(1),
(2), (4) Date: Aug. 5, 2011

(87) PCT Pub. No.: WO2010/052579
PCT Pub. Date: May 14, 2010

(65) Prior Publication Data
US 2011/0288527 A1    Nov. 24, 2011

Related U.S. Application Data

(60) Provisional application No. 61/112,463, filed on Nov. 7, 2008.

(51) Int. Cl.
*A61F 7/12* (2006.01)
*A61M 31/00* (2006.01)
(Continued)

(52) U.S. Cl.
CPC ................. *A61F 7/02* (2013.01); *A61M 5/003* (2013.01); *A61M 5/427* (2013.01);
(Continued)

(58) Field of Classification Search
CPC ..................... A61B 2018/00041; A61B 18/00; A61B 2018/00005; A61B 5/150122; A61B 18/04; A61M 2205/3368; A61M 2205/3653; A61M 5/427; A61M 5/003; A61F 7/02
USPC ........................................ 604/113, 22, 20, 66
See application file for complete search history.

(56) References Cited

U.S. PATENT DOCUMENTS 3,620,209 A   11/1971   Kravitz
3,683,911 A   8/1972    McCormick
(Continued)

FOREIGN PATENT DOCUMENTS

EP   1611848   1/2006
EP   1695664   8/2006
(Continued)

OTHER PUBLICATIONS

European Search Report for EP1315647 mailed Jul. 26, 2013.
(Continued)

*Primary Examiner* — Aarti B Berdichevsky
*Assistant Examiner* — Bradley Osinski
(74) *Attorney, Agent, or Firm* — Cooley LLP; Brian P. Hopkins

(57) ABSTRACT

A therapeutic treatment device, system and method for improving administration of a temperature sensitive drug into a tissue on the body of a patient at a drug injection site are disclosed. The device includes a treatment element with a controllable heating element in temperature communicative contact with the tissue adjacent to the drug injection site. The controllable heating element is configured to heat the tissue adjacent to the drug injection site to a controllable temperature but does not heat the injected drug above a predetermined limiting temperature, above which degradation of the injected drug may occur.

24 Claims, 4 Drawing Sheets

(51) Int. Cl.
*A61F 7/02* (2006.01)
*A61M 5/00* (2006.01)
*A61M 5/42* (2006.01)
*A61B 18/00* (2006.01)
*A61B 19/00* (2006.01)
*A61F 7/00* (2006.01)
*A61M 5/20* (2006.01)

(52) U.S. Cl.
CPC .............. *A61B 2018/00005* (2013.01); *A61B 2019/4815* (2013.01); *A61F 7/007* (2013.01); *A61F 2007/0093* (2013.01); *A61F 2007/0096* (2013.01); *A61F 2007/0226* (2013.01); *A61M 5/20* (2013.01); *A61M 2205/273* (2013.01); *A61M 2205/3368* (2013.01); *A61M 2205/3653* (2013.01); *A61M 2209/00* (2013.01)
USPC .......................................... 604/113; 604/66

(56) References Cited

U.S. PATENT DOCUMENTS

| | | |
|---|---|---|
| 4,230,105 A | 10/1980 | Harwood |
| H71 H | 6/1986 | Sorenson et al. |
| 4,628,928 A | 12/1986 | Lowell |
| 4,685,911 A | 8/1987 | Konno et al. |
| 4,744,787 A | 5/1988 | Phipps et al. |
| 4,747,819 A | 5/1988 | Phipps et al. |
| 4,771,772 A | 9/1988 | DeWitt |
| 4,898,592 A | 2/1990 | Latzke et al. |
| 4,948,587 A | 8/1990 | Kost et al. |
| 4,963,360 A | 10/1990 | Argaud |
| 4,987,897 A | 1/1991 | Funke |
| 4,998,930 A | 3/1991 | Lundahl |
| 5,047,007 A | 9/1991 | McNichols et al. |
| 5,053,033 A | 10/1991 | Clarke |
| 5,098,429 A | 3/1992 | Sterzer |
| 5,113,859 A | 5/1992 | Funke |
| 5,135,477 A | 8/1992 | Untereker et al. |
| 5,213,568 A | 5/1993 | Lattin et al. |
| 5,243,986 A | 9/1993 | Wurster |
| 5,271,736 A | 12/1993 | Picha |
| 5,306,252 A | 4/1994 | Yutori et al. |
| 5,307,816 A | 5/1994 | Hashimoto et al. |
| 5,324,521 A | 6/1994 | Gertner et al. |
| 5,332,577 A | 7/1994 | Gertner et al. |
| 5,354,324 A | 10/1994 | Gregory |
| 5,378,475 A | 1/1995 | Smith et al. |
| 5,383,873 A | 1/1995 | Hoey et al. |
| 5,411,550 A | 5/1995 | Herweck et al. |
| 5,430,016 A | 7/1995 | Balschmidt et al. |
| 5,498,254 A | 3/1996 | Hoey et al. |
| 5,512,048 A | 4/1996 | Slettenmark |
| 5,523,092 A | 6/1996 | Hanson et al. |
| 5,525,356 A | 6/1996 | Jevne et al. |
| 5,527,292 A | 6/1996 | Adams et al. |
| 5,545,208 A | 8/1996 | Wolff et al. |
| 5,556,421 A | 9/1996 | Prutchi et al. |
| 5,564,439 A | 10/1996 | Picha |
| 5,567,592 A | 10/1996 | Benet et al. |
| 5,571,152 A | 11/1996 | Chen et al. |
| 5,590,657 A | 1/1997 | Cain et al. |
| 5,591,445 A | 1/1997 | Hoey et al. |
| 5,634,468 A | 6/1997 | Platt et al. |
| 5,658,583 A | 8/1997 | Zhang et al. |
| 5,706,807 A | 1/1998 | Picha |
| 5,713,847 A | 2/1998 | Howard, III et al. |
| 5,725,017 A | 3/1998 | Elsberry et al. |
| 5,725,567 A | 3/1998 | Wolff et al. |
| 5,730,125 A | 3/1998 | Prutchi et al. |
| 5,741,211 A | 4/1998 | Renirie et al. |
| 5,798,065 A | 8/1998 | Picha |
| 5,843,051 A | 12/1998 | Adams et al. |
| 5,851,217 A | 12/1998 | Wolff et al. |
| 5,851,231 A | 12/1998 | Wolff et al. |
| 5,871,446 A | 2/1999 | Wilk |
| 5,871,535 A | 2/1999 | Wolff et al. |
| 5,882,332 A | 3/1999 | Wijay |
| 5,919,216 A | 7/1999 | Houben et al. |
| 5,919,479 A | 7/1999 | Zhang et al. |
| 5,997,468 A | 12/1999 | Wolff et al. |
| 6,004,346 A | 12/1999 | Wolff et al. |
| 6,004,927 A | 12/1999 | Benet et al. |
| 6,026,316 A | 2/2000 | Kucharczyk et al. |
| 6,028,054 A | 2/2000 | Benet et al. |
| 6,043,273 A | 3/2000 | Duhaylongsod |
| 6,060,454 A | 5/2000 | Duhaylongsod |
| 6,061,587 A | 5/2000 | Kucharczyk et al. |
| 6,087,394 A | 7/2000 | Duhaylongsod |
| 6,093,167 A | 7/2000 | Houben et al. |
| 6,101,412 A | 8/2000 | Duhaylongsod |
| 6,122,536 A | 9/2000 | Sun et al. |
| 6,125,290 A | 9/2000 | Miesel |
| 6,125,291 A | 9/2000 | Miesel et al. |
| 6,127,117 A | 10/2000 | Morris et al. |
| 6,127,410 A | 10/2000 | Duhaylongsod |
| 6,133,242 A | 10/2000 | Zalewski et al. |
| 6,134,459 A | 10/2000 | Roberts et al. |
| 6,135,978 A | 10/2000 | Houben et al. |
| 6,141,589 A | 10/2000 | Duhaylongsod |
| 6,144,866 A | 11/2000 | Miesel et al. |
| 6,152,898 A | 11/2000 | Olsen |
| 6,156,029 A | 12/2000 | Mueller |
| 6,161,047 A | 12/2000 | King et al. |
| 6,198,952 B1 | 3/2001 | Miesel |
| 6,198,966 B1 | 3/2001 | Heruth |
| 6,210,368 B1 | 4/2001 | Rogers |
| 6,228,050 B1 | 5/2001 | Olsen et al. |
| 6,228,595 B1 | 5/2001 | Morris et al. |
| 6,238,367 B1 | 5/2001 | Christiansen et al. |
| 6,245,347 B1 | 6/2001 | Zhang et al. |
| 6,247,812 B1 | 6/2001 | Miehle et al. |
| 6,254,598 B1 | 7/2001 | Edwards et al. |
| 6,261,280 B1 | 7/2001 | Houben et al. |
| 6,261,595 B1 | 7/2001 | Stanley et al. |
| 6,269,340 B1 | 7/2001 | Ford et al. |
| 6,283,949 B1 | 9/2001 | Roorda |
| 6,284,266 B1 | 9/2001 | Zhang et al. |
| 6,292,702 B1 | 9/2001 | King et al. |
| 6,296,630 B1 | 10/2001 | Altman et al. |
| 6,303,142 B1 | 10/2001 | Zhang et al. |
| 6,305,381 B1 | 10/2001 | Weijand et al. |
| 6,306,431 B1 | 10/2001 | Zhang et al. |
| 6,312,412 B1 | 11/2001 | Saied et al. |
| 6,323,184 B1 | 11/2001 | Zalewski et al. |
| 6,338,850 B1 | 1/2002 | Jevnikar et al. |
| 6,340,472 B1 | 1/2002 | Zhang et al. |
| 6,342,250 B1 | 1/2002 | Masters |
| 6,350,276 B1 | 2/2002 | Knowlton |
| 6,375,628 B1 | 4/2002 | Zadno-Azizi et al. |
| 6,377,846 B1 | 4/2002 | Chornenky et al. |
| 6,379,382 B1 | 4/2002 | Yang |
| 6,385,491 B1 | 5/2002 | Lindemans et al. |
| 6,389,313 B1 | 5/2002 | Marchitto et al. |
| 6,395,015 B1 | 5/2002 | Borst et al. |
| 6,414,018 B1 | 7/2002 | Duhaylongsod |
| 6,416,510 B1 | 7/2002 | Altman et al. |
| 6,425,853 B1 | 7/2002 | Edwards |
| 6,427,088 B1 | 7/2002 | Bowman, IV et al. |
| 6,442,435 B2 | 8/2002 | King et al. |
| 6,447,443 B1 | 9/2002 | Keogh et al. |
| 6,449,507 B1 | 9/2002 | Hill et al. |
| 6,453,195 B1 | 9/2002 | Thompson |
| 6,453,648 B1 | 9/2002 | Zhang et al. |
| 6,456,883 B1 | 9/2002 | Torgerson et al. |
| 6,458,102 B1 | 10/2002 | Mann et al. |
| 6,458,118 B1 | 10/2002 | Lent et al. |
| 6,461,329 B1 | 10/2002 | Van Antwerp et al. |
| 6,465,006 B1 | 10/2002 | Zhang et al. |
| 6,465,709 B1 | 10/2002 | Sun et al. |
| 6,471,675 B1 | 10/2002 | Rogers et al. |
| 6,471,689 B1 | 10/2002 | Joseph et al. |
| 6,482,214 B1 | 11/2002 | Sidor, Jr. et al. |
| 6,485,464 B1 | 11/2002 | Christenson et al. |

(56) References Cited

U.S. PATENT DOCUMENTS

| | | |
|---|---|---|
| 6,487,446 B1 | 11/2002 | Hill et al. |
| 6,488,959 B2 | 12/2002 | Stanley et al. |
| 6,511,428 B1 | 1/2003 | Azuma et al. |
| 6,512,958 B1 | 1/2003 | Swoyer et al. |
| 6,528,086 B2 | 3/2003 | Zhang |
| 6,532,388 B1 | 3/2003 | Hill et al. |
| 6,537,242 B1 | 3/2003 | Palmer |
| 6,542,350 B1 | 4/2003 | Rogers |
| 6,544,212 B2 | 4/2003 | Galley et al. |
| 6,546,281 B1 | 4/2003 | Zhang et al. |
| 6,551,276 B1 | 4/2003 | Mann et al. |
| 6,551,346 B2 | 4/2003 | Crossley |
| 6,554,798 B1 | 4/2003 | Mann et al. |
| 6,558,345 B1 | 5/2003 | Houben et al. |
| 6,558,382 B2 | 5/2003 | Jahns et al. |
| 6,562,001 B2 | 5/2003 | Lebel et al. |
| 6,564,105 B2 | 5/2003 | Starkweather et al. |
| 6,571,125 B2 | 5/2003 | Thompson |
| 6,572,542 B1 | 6/2003 | Houben et al. |
| 6,572,583 B1 | 6/2003 | Olsen et al. |
| 6,577,899 B2 | 6/2003 | Lebel et al. |
| 6,584,335 B1 | 6/2003 | Haar et al. |
| 6,584,360 B2 | 6/2003 | Francischelli et al. |
| 6,585,644 B2 | 7/2003 | Lebel et al. |
| 6,585,707 B2 | 7/2003 | Cabiri et al. |
| 6,592,519 B1 | 7/2003 | Martinez |
| 6,597,946 B2 | 7/2003 | Avrahami et al. |
| 6,605,039 B2 | 8/2003 | Houben et al. |
| 6,613,082 B2 | 9/2003 | Yang |
| 6,613,084 B2 | 9/2003 | Yang |
| 6,613,350 B1 | 9/2003 | Zhang et al. |
| 6,615,083 B2 | 9/2003 | Kupper |
| 6,620,151 B2 | 9/2003 | Blischak et al. |
| 6,622,731 B2 | 9/2003 | Daniel et al. |
| 6,626,867 B1 | 9/2003 | Christenson et al. |
| 6,628,987 B1 | 9/2003 | Hill et al. |
| 6,628,989 B1 | 9/2003 | Penner et al. |
| 6,635,167 B1 | 10/2003 | Batman et al. |
| 6,644,321 B1 | 11/2003 | Behm |
| 6,645,176 B1 | 11/2003 | Christenson et al. |
| 6,647,299 B2 | 11/2003 | Bourget |
| 6,648,821 B2 | 11/2003 | Lebel et al. |
| 6,650,935 B1 | 11/2003 | Watmough |
| 6,659,948 B2 | 12/2003 | Lebel et al. |
| 6,669,663 B1 | 12/2003 | Thompson |
| 6,673,070 B2 | 1/2004 | Davis et al. |
| 6,673,596 B1 | 1/2004 | Sayler et al. |
| 6,675,049 B2 | 1/2004 | Thompson et al. |
| 6,681,135 B1 | 1/2004 | Davis et al. |
| 6,685,452 B2 | 2/2004 | Christiansen et al. |
| 6,687,546 B2 | 2/2004 | Lebel et al. |
| 6,690,973 B2 | 2/2004 | Hill et al. |
| 6,694,191 B2 | 2/2004 | Starkweather et al. |
| 6,697,667 B1 | 2/2004 | Lee et al. |
| 6,706,038 B2 | 3/2004 | Francischelli et al. |
| 6,711,436 B1 | 3/2004 | Duhaylongsod |
| 6,714,822 B2 | 3/2004 | King et al. |
| 6,716,178 B1 | 4/2004 | Kilpatrick et al. |
| 6,718,208 B1 | 4/2004 | Hill et al. |
| 6,723,087 B2 | 4/2004 | O'Neill et al. |
| 6,726,673 B1 | 4/2004 | Zhang et al. |
| 6,728,574 B2 | 4/2004 | Ujhelyi et al. |
| 6,733,446 B2 | 5/2004 | Lebel et al. |
| 6,733,474 B2 | 5/2004 | Kusleika |
| 6,733,476 B2 | 5/2004 | Christenson et al. |
| 6,733,500 B2 | 5/2004 | Kelley et al. |
| 6,735,471 B2 | 5/2004 | Hill et al. |
| 6,736,789 B1 | 5/2004 | Spickermann |
| 6,736,797 B1 | 5/2004 | Larsen et al. |
| 6,738,671 B2 | 5/2004 | Christophersom et al. |
| 6,740,075 B2 | 5/2004 | Lebel et al. |
| 6,743,204 B2 | 6/2004 | Christenson et al. |
| 6,743,227 B2 | 6/2004 | Seraj et al. |
| 6,744,350 B2 | 6/2004 | Blomquist |
| 6,748,653 B2 | 6/2004 | Lindemans et al. |
| 6,752,155 B2 | 6/2004 | Behm |
| 6,755,849 B1 | 6/2004 | Gowda et al. |
| 6,756,053 B2 | 6/2004 | Zhang et al. |
| 6,758,810 B2 | 7/2004 | Lebel et al. |
| 6,758,828 B2 | 7/2004 | Hammer et al. |
| 6,764,446 B2 | 7/2004 | Wolinsky et al. |
| 6,766,183 B2 | 7/2004 | Walsh et al. |
| 6,780,426 B2 | 8/2004 | Zhang et al. |
| 6,799,149 B2 | 9/2004 | Hartlaub |
| 6,804,558 B2 | 10/2004 | Haller et al. |
| 6,805,667 B2 | 10/2004 | Christopherson et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,823,213 B1 | 11/2004 | Norris et al. |
| 6,827,702 B2 | 12/2004 | Lebel et al. |
| 6,836,687 B2 | 12/2004 | Kelley et al. |
| 6,846,823 B2 | 1/2005 | Landau et al. |
| 6,852,104 B2 | 2/2005 | Blomquist |
| 6,852,694 B2 | 2/2005 | Van Antwerp et al. |
| 6,865,419 B2 | 3/2005 | Mulligan et al. |
| 6,866,678 B2 | 3/2005 | Shenderova et al. |
| 6,872,200 B2 | 3/2005 | Mann et al. |
| 6,873,268 B2 | 3/2005 | Lebel et al. |
| 6,878,529 B2 | 4/2005 | Harrow et al. |
| 6,887,238 B2 | 5/2005 | Jahns et al. |
| 6,904,318 B2 | 6/2005 | Hill et al. |
| 6,913,763 B2 | 7/2005 | Lerner |
| 6,915,157 B2 | 7/2005 | Bennett et al. |
| 6,922,585 B2 | 7/2005 | Zhou et al. |
| 6,923,784 B2 | 8/2005 | Stein |
| 6,925,393 B1 | 8/2005 | Kalatz et al. |
| 6,927,246 B2 | 8/2005 | Noronha et al. |
| 6,928,338 B1 | 8/2005 | Buchser et al. |
| 6,930,602 B2 | 8/2005 | Villaseca et al. |
| 6,936,029 B2 | 8/2005 | Mann et al. |
| 6,950,708 B2 | 9/2005 | Bowman, IV et al. |
| 6,955,661 B1 | 10/2005 | Herweck et al. |
| 6,955,819 B2 | 10/2005 | Zhang et al. |
| 6,958,705 B2 | 10/2005 | Lebel et al. |
| 6,961,448 B2 | 11/2005 | Nichols et al. |
| 6,962,584 B1 | 11/2005 | Stone et al. |
| 6,966,322 B2 | 11/2005 | McVenes et al. |
| 6,969,369 B2 | 11/2005 | Struble |
| 6,974,437 B2 | 12/2005 | Lebel et al. |
| 6,978,174 B2 | 12/2005 | Gelfand et al. |
| 6,979,315 B2 | 12/2005 | Rogers et al. |
| 6,979,326 B2 | 12/2005 | Mann et al. |
| 6,979,351 B2 | 12/2005 | Forsell et al. |
| 6,984,229 B2 | 1/2006 | Neuberger |
| 6,985,768 B2 | 1/2006 | Hemming et al. |
| 6,991,916 B2 | 1/2006 | Benson et al. |
| 6,997,920 B2 | 2/2006 | Mann et al. |
| 7,011,630 B2 | 3/2006 | Desai et al. |
| 7,013,177 B1 | 3/2006 | Whitehurst et al. |
| 7,018,384 B2 | 3/2006 | Skakoon |
| 7,018,568 B2 | 3/2006 | Tierney |
| 7,024,236 B2 | 4/2006 | Ford et al. |
| 7,024,245 B2 | 4/2006 | Lebel et al. |
| 7,024,248 B2 | 4/2006 | Penner et al. |
| 7,025,743 B2 | 4/2006 | Mann et al. |
| 7,025,760 B2 | 4/2006 | Miller et al. |
| 7,027,856 B2 | 4/2006 | Zhou et al. |
| 7,027,871 B2 | 4/2006 | Burnes et al. |
| 7,033,338 B2 | 4/2006 | Vilks et al. |
| 7,041,704 B2 | 5/2006 | Burgard et al. |
| 7,044,082 B1 | 5/2006 | Hewett et al. |
| 7,052,483 B2 | 5/2006 | Wojcik |
| 7,054,782 B2 | 5/2006 | Hartlaub |
| 7,058,447 B2 | 6/2006 | Hill et al. |
| 7,063,684 B2 | 6/2006 | Moberg |
| 7,066,891 B2 | 6/2006 | Stadler et al. |
| 7,066,909 B1 | 6/2006 | Peter et al. |
| 7,069,078 B2 | 6/2006 | Houben |
| 7,072,802 B2 | 7/2006 | Hartlaub |
| 7,074,233 B1 | 7/2006 | Gowda et al. |
| 7,084,116 B2 | 8/2006 | Fraser et al. |
| 7,092,753 B2 | 8/2006 | Darvish et al. |

(56) References Cited

U.S. PATENT DOCUMENTS

| | | |
|---|---|---|
| 7,094,228 B2 | 8/2006 | Zhang et al. |
| 7,101,857 B2 | 9/2006 | Sung et al. |
| 7,107,086 B2 | 9/2006 | Reihl et al. |
| 7,107,093 B2 | 9/2006 | Burnes |
| 7,108,696 B2 | 9/2006 | Daniel et al. |
| 7,109,878 B2 | 9/2006 | Mann et al. |
| 7,115,606 B2 | 10/2006 | Landau et al. |
| 7,123,968 B1 | 10/2006 | Casscells, III et al. |
| 7,125,407 B2 * | 10/2006 | Edwards et al. ............... 606/41 |
| 7,125,848 B2 | 10/2006 | Fraser et al. |
| 7,133,329 B2 | 11/2006 | Skyggebjerg et al. |
| 7,149,581 B2 | 12/2006 | Goedeke |
| 7,149,773 B2 | 12/2006 | Haller et al. |
| 7,150,975 B2 | 12/2006 | Tamada et al. |
| 7,151,961 B1 | 12/2006 | Whitehurst et al. |
| 7,160,252 B2 | 1/2007 | Cho et al. |
| 7,162,303 B2 | 1/2007 | Levin et al. |
| 7,162,307 B2 | 1/2007 | Patrias |
| 7,163,511 B2 | 1/2007 | Conn et al. |
| 7,164,948 B2 | 1/2007 | Struble et al. |
| 7,167,743 B2 | 1/2007 | Heruth et al. |
| 7,171,263 B2 | 1/2007 | Darvish et al. |
| 7,171,274 B2 | 1/2007 | Starkweather et al. |
| 7,179,226 B2 | 2/2007 | Crothall et al. |
| 7,181,505 B2 | 2/2007 | Haller et al. |
| 7,184,828 B2 | 2/2007 | Hill et al. |
| 7,184,829 B2 | 2/2007 | Hill et al. |
| 7,186,247 B2 | 3/2007 | Ujhelyi et al. |
| 7,187,979 B2 | 3/2007 | Haubrich et al. |
| 7,190,997 B1 | 3/2007 | Darvish et al. |
| 7,191,008 B2 | 3/2007 | Schmidt et al. |
| 7,193,521 B2 | 3/2007 | Moberg et al. |
| 7,203,541 B2 | 4/2007 | Sowelam et al. |
| 7,206,632 B2 | 4/2007 | King |
| 7,209,784 B2 | 4/2007 | Schmidt |
| 7,209,790 B2 | 4/2007 | Thompson et al. |
| 7,218,964 B2 | 5/2007 | Hill et al. |
| 2001/0022279 A1 | 9/2001 | Denyer et al. |
| 2001/0047195 A1 | 11/2001 | Crossley |
| 2002/0026141 A1 | 2/2002 | Houben et al. |
| 2002/0032406 A1 | 3/2002 | Kusleika |
| 2002/0038101 A1 | 3/2002 | Avrahami et al. |
| 2002/0040208 A1 | 4/2002 | Flaherty et al. |
| 2002/0068869 A1 | 6/2002 | Brisken et al. |
| 2002/0072743 A1 | 6/2002 | KenKnight et al. |
| 2002/0077673 A1 | 6/2002 | Penner et al. |
| 2002/0082583 A1 | 6/2002 | Lerner |
| 2002/0082665 A1 | 6/2002 | Haller et al. |
| 2002/0102707 A1 | 8/2002 | Harrow et al. |
| 2002/0106410 A1 | 8/2002 | Masters |
| 2002/0133148 A1 | 9/2002 | Daniel et al. |
| 2002/0137014 A1 | 9/2002 | Anderson et al. |
| 2002/0176849 A1 | 11/2002 | Slepian |
| 2002/0177689 A1 | 11/2002 | Benson et al. |
| 2002/0177772 A1 | 11/2002 | Altman et al. |
| 2002/0177782 A1 | 11/2002 | Penner |
| 2002/0183682 A1 | 12/2002 | Darvish et al. |
| 2002/0183686 A1 | 12/2002 | Darvish et al. |
| 2003/0028089 A1 | 2/2003 | Galley et al. |
| 2003/0040683 A1 | 2/2003 | Rule et al. |
| 2003/0060753 A1 | 3/2003 | Starkweather et al. |
| 2003/0060765 A1 | 3/2003 | Campbell et al. |
| 2003/0069614 A1 | 4/2003 | Bowman et al. |
| 2003/0073609 A1 | 4/2003 | Pinkerton |
| 2003/0100885 A1 | 5/2003 | Pettis et al. |
| 2003/0130616 A1 | 7/2003 | Steil et al. |
| 2003/0144712 A1 | 7/2003 | Streeter |
| 2003/0167033 A1 | 9/2003 | Chen et al. |
| 2003/0171401 A1 | 9/2003 | Johnson et al. |
| 2003/0176933 A1 | 9/2003 | Lebel et al. |
| 2003/0181852 A1 | 9/2003 | Mann et al. |
| 2003/0181894 A1 | 9/2003 | Neuberger |
| 2003/0187525 A1 | 10/2003 | Mann et al. |
| 2003/0191431 A1 | 10/2003 | Mann et al. |
| 2003/0195462 A1 | 10/2003 | Mann et al. |
| 2003/0208152 A1 | 11/2003 | Avrahami et al. |
| 2003/0212364 A1 | 11/2003 | Mann et al. |
| 2003/0212441 A1 | 11/2003 | Starkweather et al. |
| 2003/0231990 A1 | 12/2003 | Faries et al. |
| 2004/0014131 A1 | 1/2004 | Benson et al. |
| 2004/0024361 A1 | 2/2004 | Fago et al. |
| 2004/0028707 A1 | 2/2004 | Pinkerton |
| 2004/0030282 A1 | 2/2004 | Freyman et al. |
| 2004/0059328 A1 | 3/2004 | Daniel et al. |
| 2004/0062148 A1 | 4/2004 | Skyggebjerg et al. |
| 2004/0063200 A1 | 4/2004 | Chaikof et al. |
| 2004/0064086 A1 | 4/2004 | Gottlieb et al. |
| 2004/0064127 A1 | 4/2004 | Lerner |
| 2004/0064133 A1 | 4/2004 | Miller et al. |
| 2004/0073190 A1 | 4/2004 | Deem et al. |
| 2004/0082639 A1 | 4/2004 | Ho et al. |
| 2004/0085215 A1 | 5/2004 | Moberg et al. |
| 2004/0092885 A1 | 5/2004 | Duchon et al. |
| 2004/0098113 A1 | 5/2004 | Forsell et al. |
| 2004/0111132 A1 | 6/2004 | Shenderova et al. |
| 2004/0127895 A1 | 7/2004 | Flock et al. |
| 2004/0142034 A1 | 7/2004 | Thor et al. |
| 2004/0147872 A1 | 7/2004 | Thompson |
| 2004/0157884 A1 | 8/2004 | Johnson et al. |
| 2004/0171518 A1 | 9/2004 | Van Antwerp et al. |
| 2004/0186533 A1 | 9/2004 | Greenberg et al. |
| 2004/0193090 A1 | 9/2004 | Lebel et al. |
| 2004/0198822 A1 | 10/2004 | Fraser et al. |
| 2004/0202692 A1 | 10/2004 | Shanley et al. |
| 2004/0204683 A1 * | 10/2004 | McGuckin et al. ............ 604/173 |
| 2004/0209869 A1 | 10/2004 | Landau et al. |
| 2004/0209960 A1 | 10/2004 | Burgard et al. |
| 2004/0210267 A1 | 10/2004 | Lebel et al. |
| 2004/0220551 A1 | 11/2004 | Flaherty et al. |
| 2004/0225338 A1 | 11/2004 | Lebel et al. |
| 2004/0230117 A1 | 11/2004 | Tosaya et al. |
| 2004/0236269 A1 | 11/2004 | Marchitto et al. |
| 2004/0248979 A1 | 12/2004 | Brettman et al. |
| 2004/0260239 A1 | 12/2004 | Kusleika |
| 2004/0265353 A1 | 12/2004 | Zhang et al. |
| 2005/0004663 A1 | 1/2005 | Llanos et al. |
| 2005/0008580 A1 | 1/2005 | Gong et al. |
| 2005/0009735 A1 | 1/2005 | Kim et al. |
| 2005/0015055 A1 | 1/2005 | Yang |
| 2005/0020577 A1 | 1/2005 | Landau et al. |
| 2005/0026909 A1 | 2/2005 | Landau et al. |
| 2005/0033148 A1 | 2/2005 | Haueter et al. |
| 2005/0033231 A1 | 2/2005 | Powell |
| 2005/0033370 A1 | 2/2005 | Jelen et al. |
| 2005/0054725 A1 | 3/2005 | Thor et al. |
| 2005/0059938 A1 | 3/2005 | Malisch |
| 2005/0065464 A1 | 3/2005 | Talbot et al. |
| 2005/0065465 A1 | 3/2005 | Lebel et al. |
| 2005/0065556 A1 | 3/2005 | Reghabi et al. |
| 2005/0084477 A1 | 4/2005 | Van Antwerp et al. |
| 2005/0090866 A1 | 4/2005 | Miller et al. |
| 2005/0107353 A1 | 5/2005 | Burgard et al. |
| 2005/0107738 A1 | 5/2005 | Slater et al. |
| 2005/0107743 A1 | 5/2005 | Fangrow |
| 2005/0113798 A1 | 5/2005 | Slater et al. |
| 2005/0124560 A1 | 6/2005 | Sung et al. |
| 2005/0137670 A1 | 6/2005 | Christopherson et al. |
| 2005/0143636 A1 | 6/2005 | Zhang et al. |
| 2005/0148955 A1 | 7/2005 | Chong et al. |
| 2005/0171160 A1 | 8/2005 | Edgar et al. |
| 2005/0171513 A1 | 8/2005 | Mann et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182463 A1 | 8/2005 | Hunter et al. |
| 2005/0183731 A1 | 8/2005 | Hunter et al. |
| 2005/0186244 A1 | 8/2005 | Hunter et al. |
| 2005/0187140 A1 | 8/2005 | Hunter et al. |
| 2005/0192637 A1 | 9/2005 | Girouard et al. |
| 2005/0196421 A1 | 9/2005 | Hunter et al. |
| 2005/0208095 A1 | 9/2005 | Hunter et al. |
| 2005/0217674 A1 | 10/2005 | Burton et al. |
| 2005/0220836 A1 | 10/2005 | Falotico et al. |

(56) References Cited

U.S. PATENT DOCUMENTS

| | | |
|---|---|---|
| 2005/0221270 A1 | 10/2005 | Connelly et al. |
| 2005/0222191 A1 | 10/2005 | Falotico et al. |
| 2005/0228049 A1 | 10/2005 | Thor et al. |
| 2005/0229931 A1 | 10/2005 | Denyer et al. |
| 2005/0232964 A1 | 10/2005 | Fennimore |
| 2005/0232965 A1 | 10/2005 | Falotico |
| 2005/0239838 A1 | 10/2005 | Edgar et al. |
| 2005/0239890 A1 | 10/2005 | Fraser et al. |
| 2005/0245840 A1 | 11/2005 | Christopherson et al. |
| 2005/0249775 A1 | 11/2005 | Falotico et al. |
| 2005/0249776 A1 | 11/2005 | Chen et al. |
| 2005/0256165 A1 | 11/2005 | Edgar et al. |
| 2005/0256499 A1 | 11/2005 | Pettis et al. |
| 2005/0267550 A1 | 12/2005 | Hess et al. |
| 2005/0270245 A1 | 12/2005 | Villaseca et al. |
| 2005/0272719 A1 | 12/2005 | Landau et al. |
| 2005/0272806 A1 | 12/2005 | Falotico et al. |
| 2005/0276842 A1 | 12/2005 | Zhang et al. |
| 2005/0282799 A1 | 12/2005 | Landau et al. |
| 2005/0282859 A1 | 12/2005 | Thor |
| 2006/0025663 A1 | 2/2006 | Talbot et al. |
| 2006/0025756 A1 | 2/2006 | Francischelli et al. |
| 2006/0030837 A1 | 2/2006 | McKenna et al. |
| 2006/0030838 A1 | 2/2006 | Gonnelli |
| 2006/0031094 A1 | 2/2006 | Cohen et al. |
| 2006/0063754 A1 | 3/2006 | Edgar et al. |
| 2006/0063755 A1 | 3/2006 | Edgar et al. |
| 2006/0063928 A1 | 3/2006 | Edgar et al. |
| 2006/0079858 A1 | 4/2006 | Miller et al. |
| 2006/0079941 A1 | 4/2006 | Ovsyshcher et al. |
| 2006/0094705 A1 | 5/2006 | Edgar et al. |
| 2006/0111704 A1 | 5/2006 | Brenneman et al. |
| 2006/0122666 A1 | 6/2006 | Nghiem et al. |
| 2006/0122863 A1 | 6/2006 | Gottesman et al. |
| 2006/0129050 A1 | 6/2006 | Martinson et al. |
| 2006/0129225 A1 | 6/2006 | Kopia et al. |
| 2006/0142819 A1 | 6/2006 | Penner et al. |
| 2006/0149218 A1 | 7/2006 | Slater et al. |
| 2006/0149339 A1 | 7/2006 | Burnes et al. |
| 2006/0173406 A1 | 8/2006 | Hayes et al. |
| 2006/0173444 A1 | 8/2006 | Choy et al. |
| 2006/0184092 A1 | 8/2006 | Atanasoska et al. |
| 2006/0184154 A1 | 8/2006 | Moberg et al. |
| 2006/0188575 A1 | 8/2006 | Thor et al. |
| 2006/0247311 A1 | 11/2006 | Fraser et al. |
| 2006/0253085 A1 | 11/2006 | Geismar et al. |
| 2006/0264509 A1 | 11/2006 | Fraser et al. |
| 2006/0264894 A1 | 11/2006 | Moberg et al. |
| 2006/0270968 A1 | 11/2006 | Greenberg et al. |
| 2006/0271020 A1 | 11/2006 | Huang et al. |
| 2006/0271112 A1 | 11/2006 | Martinson et al. |
| 2006/0272652 A1 | 12/2006 | Stocker et al. |
| 2006/0276542 A1 | 12/2006 | Fraser et al. |
| 2006/0293309 A1 | 12/2006 | Thor et al. |
| 2007/0003549 A1 | 1/2007 | Ignatovich et al. |
| 2007/0004752 A1 | 1/2007 | Coughlin et al. |
| 2007/0009956 A1 | 1/2007 | Srinivas et al. |
| 2007/0016163 A1 | 1/2007 | Santini et al. |
| 2007/0016170 A1 | 1/2007 | Kovelman |
| 2007/0026042 A1 | 2/2007 | Narayanan |
| 2007/0030764 A1 | 2/2007 | Skyggebjerg et al. |
| 2007/0033074 A1 | 2/2007 | Nitzan et al. |
| 2007/0038100 A1 | 2/2007 | Nita |
| 2007/0040449 A1 | 2/2007 | Spurlin et al. |
| 2007/0048350 A1 | 3/2007 | Falotico et al. |
| 2007/0051362 A1 | 3/2007 | Sullivan et al. |
| 2007/0053996 A1 | 3/2007 | Boyden et al. |
| 2007/0054319 A1 | 3/2007 | Boyden et al. |
| 2007/0054871 A1 | 3/2007 | Pastore et al. |
| 2007/0060652 A1 | 3/2007 | Fraser et al. |
| 2007/0060864 A1 | 3/2007 | Redding |
| 2007/0060871 A1 | 3/2007 | Istoc et al. |
| 2007/0083258 A1 | 4/2007 | Falotico et al. |
| 2007/0087315 A1 | 4/2007 | Stuart et al. |
| 2007/0088248 A1 | 4/2007 | Glenn et al. |
| 2007/0093752 A1 | 4/2007 | Zhao et al. |
| 2007/0098753 A1 | 5/2007 | Falotico et al. |
| 2007/0112298 A1 | 5/2007 | Mueller et al. |
| 2007/0219480 A1 | 9/2007 | Kamen et al. |
| 2008/0023593 A1 | 1/2008 | Ritota et al. |
| 2008/0200897 A1 | 8/2008 | Hoss et al. |
| 2008/0281297 A1 | 11/2008 | Pesach et al. |
| 2010/0057003 A1 | 3/2010 | Dos Santos |
| 2010/0106088 A1 | 4/2010 | Yodfat et al. |
| 2010/0152644 A1 | 6/2010 | Pesach et al. |
| 2010/0174225 A1 | 7/2010 | Pesach et al. |
| 2010/0286467 A1 | 11/2010 | Pesach et al. |
| 2010/0292557 A1 | 11/2010 | Pesach et al. |
| 2010/0318035 A1 | 12/2010 | Edwards et al. |
| 2011/0184342 A1 | 7/2011 | Pesach et al. |

FOREIGN PATENT DOCUMENTS

| | | |
|---|---|---|
| EP | 1752174 A1 | 2/2007 |
| FR | 2795629 | 1/2001 |
| WO | WO-00/18339 | 4/2000 |
| WO | WO-00/23132 | 4/2000 |
| WO | WO-00/32259 | 6/2000 |
| WO | WO-00/74763 | 12/2000 |
| WO | WO-00/78212 A1 | 12/2000 |
| WO | WO-01/01852 | 1/2001 |
| WO | WO-01/47408 | 7/2001 |
| WO | WO-01/93931 | 12/2001 |
| WO | WO-02/068028 | 9/2002 |
| WO | WO-03/055384 | 7/2003 |
| WO | WO-03/086534 | 10/2003 |
| WO | WO-2006/049570 A2 | 5/2006 |
| WO | WO-2006/084464 | 8/2006 |
| WO | WO-2006/091650 A2 | 8/2006 |
| WO | WO-2008/051924 A2 | 5/2008 |
| WO | WO-2008/114218 | 9/2008 |
| WO | WO-2008/114220 | 9/2008 |
| WO | WO-2008/114223 | 9/2008 |
| WO | WO-2008/114224 | 9/2008 |
| WO | WO-2009/081262 | 7/2009 |
| WO | WO-2010/052579 | 5/2010 |

OTHER PUBLICATIONS

Belinda et. al., (1996), Journal of Physiology, 572.3:811-820.
Bos et al., Biomaterials (2005), 26:3901-3909.
Clarke et. al., (2005), Diabetes Care, 28:2412-2417.
Facchinetti et. al., (2007), Journal of Diabetes Science and Technology, 1:617-623.
Heinemann, (2002), Diabetes Technology & Therapeutics, 5:673-682.
Koivisto et al. (1980), British Medical Journal, 280:1411-1413.
Koivisto et al., (1978), The New England Journal of Medicine, 298:79-83.
Magerl et. al., (1996), Journal of Physiology, 497:837-848.
Midttun et. al., (1996), Clinical Physioloy, 16:259-274.
Rebrin et al., (2000), Diabetes Technology and Therapeutics, 2:461-472.
Shumaker et al., (2006), Lasers in Surgery and Medicine, 38:211-217.
Sindelka et al., (1994), Diabetologia, 37:377-380.

\* cited by examiner

DEVICE AND METHOD FOR DRUG DELIVERY

CROSS-REFERENCE TO RELATED APPLICATIONS

The present application claims priority to International Patent Application No. PCT/IB2009/007600, to Benny Pesach et al., filed Nov. 6, 2009, and entitled "DEVICE AND METHOD FOR DRUG DELIVERY", which claims priority to U.S. Provisional Patent Application No. 61/112,463, filed on Nov. 7, 2008, the disclosures of which are incorporated herein by reference in their entireties.

FIELD OF THE INVENTION

In general, the present invention relates to systems and methods for delivering drugs to a patient. In particular, embodiments of the present invention relate to systems and methods for subcutaneous injection of a medicament and using one or more treatment sources to improve effectiveness of the injected drugs.

BACKGROUND OF THE INVENTION

Drug injection by syringe, pen injectors and other devices are used regularly for subcutaneous injections of therapeutic fluids, drugs, proteins, and other compounds. Such delivery systems and methods are used also routinely for insulin delivery. In conventional insulin injection pens, the pen is typically configured to include a disposable insulin reservoir and a disposable needle through which insulin is injected into the tissue. The needle is for single use, while the insulin reservoir can be used for two to three days.

In many instances, the patients require insulin injection around the clock to keep proper levels of glucose in their blood. Two major types of insulin can be injected—long-acting insulin that provides the basal insulin rate needed for keeping patient's blood glucose in the desired range between meals and over night and an insulin bolus injection that provides an amount of insulin for matching a dose of carbohydrates consumed by the patient during meals.

When a patient consumes food, his or her levels of glucose rise. Unfortunately, many conventional subcutaneous injection devices are incapable of quickly matching or preventing the rise of blood glucose. The delay in such matching is also true in case of the "rapid-acting" insulin. Some of the reasons for this delay include a lag in the absorption of insulin from the injection site and the time it takes for complex insulin molecules to break down into monomers.

Additionally, since blood glucose levels rise shortly following the meal, the delay in matching insulin to the rising levels causes post prandial hyperglycemic events (i.e., when levels of blood glucose are above normal) to occur. Further, occasionally after a certain period of time passes (e.g., 2-3 hours) after a meal, the blood glucose levels drop yet insulin concentrations in the blood rise followed by the peak of the systemic insulin effect and may result in causing hypoglycemic events (i.e., when levels of blood glucose are below normal) to occur. Both hyperglycemic and hypoglycemic events are highly undesirable. Additionally, since local blood perfusion at the insulin injection region has large variability, depending on the ambient temperature and other parameters, it induces large variations to the delay of the peak of time profile of the insulin action. Those variations in the insulin peak action period further increase the variability in the blood glucose level.

Therefore, it is desirable to provide a system and a method that provides efficient and rapid injection and absorption of a drug to the patient circulatory system. In particular, it is desirable to provide a system and a method for injection of insulin to the patient that improves effectiveness of insulin in the blood to maintain normal levels of blood glucose and prevent or reduce hyperglycemic and hypoglycemic events.

SUMMARY OF THE INVENTION

In some embodiments, the present invention relates to systems, devices and methods for injecting drug(s), substances and/or chemicals into a patient having a tissue treatment element for improving effectiveness of drug delivery upon injection. The device, according to some embodiments of the present invention, provides for a device for improving performance of drug delivery by injections. Optionally, some embodiments of the present invention provide for a device that further provides an additional treatment to a tissue region where the drug is delivered. The treatment can be utilized to improve drug delivery process by improving the drug's pharmacokinetic ("PK") and/or pharmacodynamic ("PD") profile. The treatment may include but is not limited to methods and devices described in PCT/IB2008/051049 and in PCT/IB2008/051044, disclosures of which are incorporated herein by reference in their entireties. Optionally, the treatment may come in various forms, for example, including an analgesic, vasodilator, or the like. Optionally, the treatment may be any form of treatment that leads to an improved vasodilatation of the tissue being injected, where the treatment, includes but is not limited to, exposing the tissue region to an energy, radiation, heat, mechanical vibrations, suction, massaging, acoustic stimulation, electrical stimulation, injection of an additional substance(s), or any combination of the above to improve drug's pharmacokinetic and for pharmacodynamic profile. Each treatment type can be configured to have a separate protocol in order to evoke the necessary reaction such as vasodilatation or the like.

In some embodiments, the applied treatment induces vasodilatation through neural stimulation of the tissue around the drug injection site. The neural stimulation can be induced by thermal stimulation. The human neural response to thermal stimulation includes several mechanisms such as the Nociceptive Axon Reflex that induce vasodilatation among other effects.

In some embodiments, the induced neural response, such as the nociceptive axon reflex, also optionally induces widening of the capillary pores and increasing the capillary wall permeability. This effect is also significant for improving the absorption of the drag through the capillary wall.

In some embodiments, the applied treatment may lead to a reduction in the variability of the drug absorption in the blood or lymph system and its local and systemic effects. For example, heating the tissue region in the vicinity of the area of drug delivery to a preset regulated temperature during and/or after the drug injection and absorption into the blood may cause local blood perfusion at that region to become more reproducible and the drug absorption process more uniform and reproducible as well. Also, by reducing the delay between drug injection into the tissue and absorption into the blood system, the variability of drug action induced by the delayed profile can be reduced. In some embodiments, the temperature of the region adjacent to the injection region can be regulated for longer periods, but the cost may be the energy source volume and weight. Thus, for minimization of the energy source size the heating period or heating temporal profile can be optimized in relation to the period of the drug injection and absorption into the blood. In some embodiments of the present invention, the treatment can be tuned according to the injected insulin dose and/or type. For instance, in case of heating the vicinity of the injection site the heating period for larger insulin dose can be longer to allow rapid absorption of the larger insulin dose.

In some embodiments, a drug's temperature sensitivity can be accounted for so as to avoid protein denaturisation. In some embodiments, the delivered drug is insulin. Insulin is a temperature-sensitive protein. Thus, to avoid damage to insulin during the treatment protocol, heat can be limited so as to ensure efficacy of the delivered drug. The treatment protocol can be configured to control the temperature or the location of the treatment delivery site so as to not damage the drug. For instance, heating some types of insulin above 37° C. might damage it. Thus, the tissue around the injection site can be heated to induce the required neural response without heating the insulin itself above 37° C. For example heating the tissue at a distance of 10 mm around the injection site to 38.5° C. provides a significant vasodilatation without heating the injected insulin above 37° C.

In some embodiments, the present invention relates to method and device for improving clinical outcome of IDDM patient by combining injection of rapid acting insulin analog with heating the skin at least 1 cm apart of the infusion site to 37-39° C. for a period of 30-60 min after the injection. This combination is be configured to provide a significant improvement of the insulin PK and PD without heating the injected insulin above 37° C.

In some instances, instead of using rapid acting insulin, a mixed formulation (a mix of at least two insulin formulations with different absorption times, such as rapid acting insulin analog and regular insulin) can be used to provide both the fast absorption of the rapid acting insulin analog at the initial phase of the insulin absorption (such as 0-90 minutes from insulin injection) and then slower pharmacokinetics of the insulin action at the second phase of the insulin action (such as 90-200 min). This combination can be more beneficial, for instance, for fat reach meals in which the time that takes the food to be digested and the blood glucose excursion to diminish is longer.

In some embodiments, the present invention relates to a therapeutic treatment device for improving administration of a temperature sensitive drug into a tissue on the body of a patient at a drug injection site. The device includes a treatment element with a controllable heating element in temperature communicative contact with the tissue adjacent to the drug injection site. The controllable heating element is configured to heat the tissue adjacent to the drug injection site to a controllable temperature but does not heat the injected drug above a predetermined limiting temperature, above which degradation of the injected drug may occur.

In some embodiments, the present invention relates to a device for injection of a drug into a tissue on the body of a patient at a drug injection site. The device includes a housing for housing an injector for injecting the drug to an injection site, and a treatment element for providing an additional treatment at the drug injection site.

In some embodiments, the present invention relates to a method for administering a temperature sensitive drug into a tissue on the body of a patient at a drug injection site using a treatment device including a treatment element having a controllable heating element. The method includes placing the treatment element in temperature communicative contact with tissue on the body of the patient; administering the drug to the tissue while applying treatment to the tissue; and controlling the temperature provided by the treatment element up to a predetermined maximum temperature to prevent heating the drug above a predetermined limiting temperature, above which degradation of the drug may occur.

In some embodiments, the present invention relates to a method for treating a patient using a treatment device including a pen injector and a treatment element having a controllable treatment element. The method includes injecting a drug into a tissue on the body of the patient at a drug injection site using the pen injector; and using the treatment element, applying a treatment to the drug injection site before, during or after the injecting.

BRIEF DESCRIPTION OF THE DRAWINGS

For a better understanding of the present invention, including the various objects and advantages thereof, reference is made to the following description, which is to be taken in conjunction with the accompanying illustrative drawings.

DETAILED DESCRIPTION OF THE INVENTION

FIGS. 1-6, along with the following discussion, illustrate various exemplary embodiments of the present invention. As can be understood by one skilled in the art, the present invention is not limited to the embodiments illustrated in FIGS. 1-6 and these figures are presented for discussion purposes only.

Figure 1:
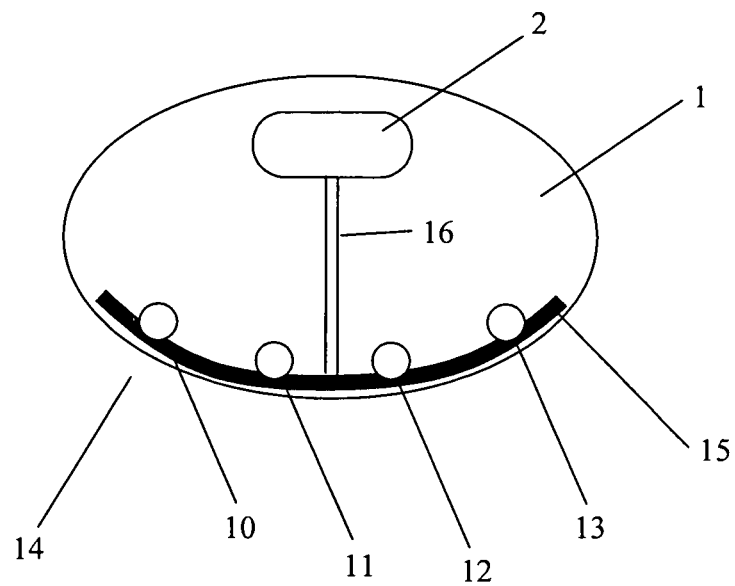
FIG. 1 illustrates an exemplary system for delivering drugs to a patient having a treatment element, according to some embodiments of the present invention.

FIG. 1 illustrates an exemplary drug delivery system, according to some embodiments of the present invention. In some embodiments of the present invention, the drug delivery system includes a treatment element that is configured to be a heating pad 1 used for four drug injections, as shown at FIG. 1. As can be understood by one skilled in the art, the number of drug injections or drug injection locations is not limited to four and can be any other number. The treatment element includes a processor and power source unit 2 (e.g., batteries) wired using electrical wires 16 to a heating element 15. As shown in FIG. 1, reference numerals 10-13 on the heating pad indicate possible recommended locations for injection of four different drug injection occasions. Heating element 15 can be configured to include a heater to heat the tissue close and/or adjacent to an injection site 14 to a temperature that improves drug's pharmacokinetics and pharmacodynamics. In case of temperature sensitive drugs, such as insulin, heating element 15 can include a heater to heat the tissue around the injection site to a temperature that improves drug's pharmacokinetics and pharmacodynamics, without heating the drug above a limiting temperature that may degrade it, such as 37° C. in the case of some types of insulin. Heating pad 1 may also include an adhesive layer on its bottom side covered with a laminate before attachment to the body. In some embodiments, the heating pad can include a temperature sensor that provides temperature information to a processor to control the heating element to stabilize the heated tissue temperature to a required temperature.

Figure 3:
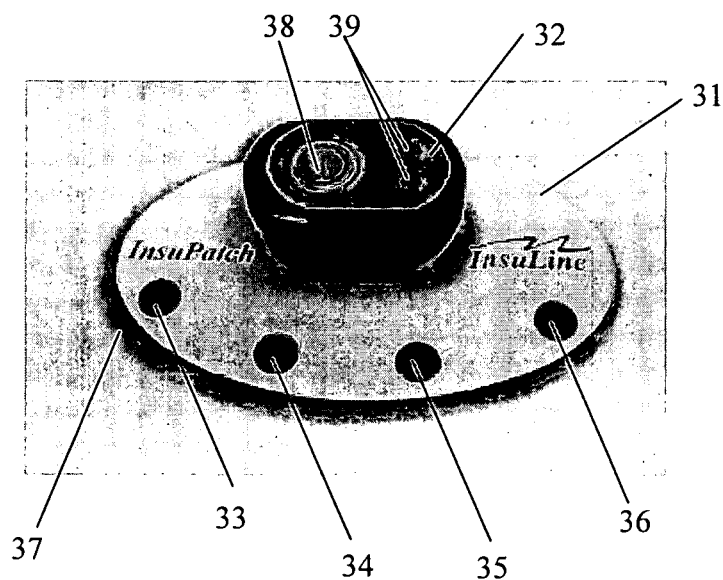
FIG. 3 illustrates an exemplary heating pad, according to some embodiments of the present invention.

A more detailed illustration of an exemplary heating pad for four injections is shown at FIG. 3. In this embodiment, the heating pad includes a disposable unit 31 and a reusable unit 32 connected by an electrical connector. In some embodiments, the reusable unit 32 can be configured to include a processor and a rechargeable power source, a button 38 for starting heating and LED indicators 39 (for example, green and yellow colored LEDs). The disposable unit 31 includes heating element (not shown in FIG. 3) and four reference numerals 33-36 indicating possible recommended locations for injections for four different drug injection occasions.

The heating pad illustrated in FIG. 3 can be used for example for one day of insulin injections. It can be attached to the abdomen or other locations used for insulin injections when the first injection should be taken. Before attachment to the body, the reusable part 32 is connected to the disposable unit 31. In some embodiments, the patient can fold his skin at the injection site using the disposable unit 31, which is flexible. The disposable unit 31 enables the patient to inject four injections at four different locations as some diabetes patients may be required to do. The possible recommended injection sites are marked by four reference numerals 33-36, such that the injection is performed near one of the locations 33-36. For instance, reference numeral 33 indicates that the insulin is injected near a skin location 37. A typical procedure for insulin injection for both insulin syringes and insulin pens involves: (1) folding the skin between the thumb and the index finger of one hand, thereby raising the skin; (2) performing the injection into the folded raised skin using the other hand; and (3) after the injection, releasing the skin. This is done for safety purposes in order to prevent insulin injection into a location that is too deep in the body. Using the present invention's heating pad, this procedure can be implemented by (1) placing a thumb finger on the location indicated by reference numeral 33 and an index finger few centimeters below the reference numeral 33; (2) folding the skin between the fingers; (3) performing an injection into the skin between the thumb and index fingers; (4) releasing the skin after the injection. Reference numerals 33-36 can be indicated using numbers, different color markings, and/or names of meals, such as, breakfast, lunch dinner, supper, and/or in any other fashion. In some embodiments, a short time before or after the injection, the button 38 can be pressed by the patient to start the heating for a predetermined period of time and at a predetermined temperature profile. For instance, the device can perform heating for approximately 30 min to approximately 38.5° C. In some embodiments, the patient can start heating before injection (such as, 15 min prior to injection) to maximize the effect. In some embodiments, the controller can have a delay before starting the heating. After the heating ends, the patient can leave the heating pad attached until the next insulin injection is needed. In some embodiments, the heating pad further includes a temperature sensor for providing temperature information to a controller in the reusable part 32. The temperature sensor is embedded in the disposable part 31 with good heat conduction to the heated tissue and/or to heating element. The sensor is further configured to be connected through the electrical connector to the reusable part 32. In some embodiments, to reduce the cost of the disposable part 31, the temperature sensor can be embedded in the reusable part 32 in heat communication with the heat conductive element disposed in the disposable part 31. The temperature sensor can also be configured to measure temperature of the heated tissue with a good enough accuracy in order to control its temperature. In some embodiments, the heat conductive element can be a metal strip, such as copper, aluminum and/or any other suitable metal or combination thereof, disposed at the bottom of a disposable sticker with good heat conduction to the heated tissue and/or heating element.

In some embodiments, the patient can detach the reusable part 32 from the disposable part 31, which is kept adhered to the patient's body. In this embodiment, a smaller battery can be disposed inside the reusable part 32 for providing power for one injection. Thus, the size and weight of the reusable part 32 is reduced. In some embodiments, the battery disposed inside the reusable part 32 is capable of providing power for treatment of multiple injections (e.g., four injections, as shown in FIG. 3). In some embodiments, when the reusable and disposable parts are connected, the controller is configured to perform a system test and transmit the results of the test to the user by lighting LED indicators 39 in a predetermined manner. For example, a green-lit LED indicator 39 indicates that the device is functioning normally and a yellow lit LED indicator 39 indicates that the heating pad/controller may be malfunctioning. In some embodiments, the LED indicators 39 can be used for indicating a heating operation (i.e., green lit LED is on), a low battery (i.e., a yellow lit LED is flashing), and any fault or misuse indication (i.e., yellow lit LED is on).

In some embodiments, the heating pad can be configured to have an automatic operating cycle by identifying the timing of the injection and starting the heating profile accordingly. The injection detection can be performed by detecting folding of the skin using a pressure and/or mechanical sensor that can be placed in the disposable part 31 (shown in FIG. 3). Alternatively, a pressure sensor can be placed at or on marking(s)/location(s) indicated by the reference numerals 33-36 (shown in FIG. 3), which can be pressed during injection. Also, injection detection can be performed using a proximity detection of the injection device, such as, an injection pen or a syringe. In case of different markings on the disposable part 31 for different meals, the detection of the pressure on the marking related to a specific meal can indicate to the processor the type of meal is being consumed (e.g., breakfast, lunch, dinner, etc.), thereby causing the processor to invoke an appropriate heating profile that is optimized for the specific meal. Another alternative to get specific meal information is to add a real-time clock to the processing unit and use the time of the day information to decide upon the optimal treatment to apply. In some embodiments, disposable part 31 can have different markings according to meal contents, such as, carbohydrate-reach meal, fat-reach meal, etc., and the processor can be configured to identify the pressed marking and fit the optimal heat profile accordingly. In embodiments of meal-specific or meal-content-specific or dose-specific markings, various methods for indentifying the injection location can also be used to identify the injection location and to apply the optimal treatment accordingly. The proximity detection can be done also using RF detection by having RFID chip mounted on injection device, or optical detection or other methods known in the art. In some embodiments, the processor can be configured to alert the user in the event that the user attempts to inject insulin to a previously used injection site, such as, when the user presses the same marking on the disposable part 31 before the injection. The alert can be aural, visual and/or any other type or combination thereof.

Figure 4:
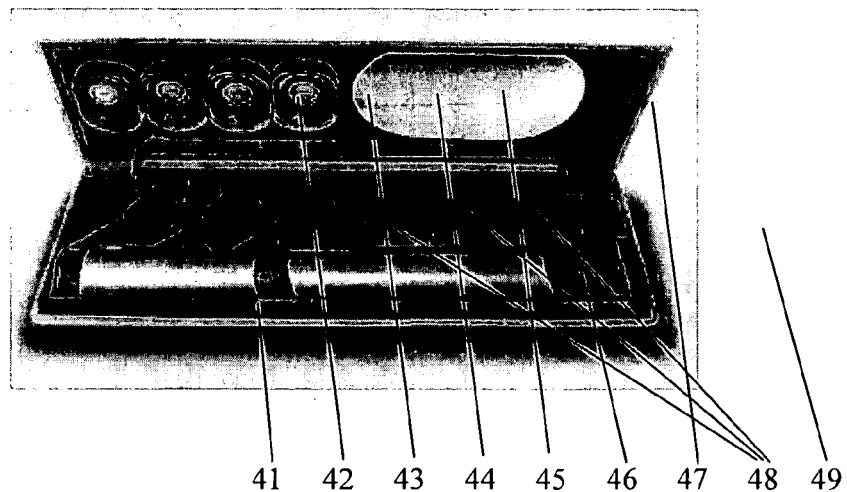
FIG. 4 illustrates an exemplary kit including a system for delivering drugs to a patient, according to some embodiments of the present invention.

In some embodiments, a kit including components for carrying out various embodiments of the present invention can be provided. An example of this kit is illustrated at FIG. 4.

Accordingly, in some embodiments, the kit can include an injection device and a plurality of treatment elements. For example, a case 41 can include an injection pen 46, one more reusable units 42-46, one more disposable units 47, a space for needles 48 and a space for an additional vile(s) of insulin 49. The patient can take this kit/case with her/him wherever s/he goes, thus, whenever s/he needs to get an insulin injection the kit/case contains everything necessary to carry out such injection.

In some embodiments, the reusable unit's power source can be rechargeable and can be charged using the case 41. For example, after completion of the treatment, the user can put the power source back into the case and into an electrical contact configured to charge the power source. In this embodiment, the case 41 can have a power source by itself for charging the reusable units 42-46. The power source of the case 41 can also have a rechargeable battery, which can be charged during the nights (or at any other time) by placing the case 41 in a charging cradle for recharging or connecting a designated connector on the case to charger.

In some embodiments, the case 41 can include several reusable units for a single injection (e.g., a single day use) and one or more for several injections (e.g., four injections). In some embodiments, the "reusable units" which can include the power source and controller, can be disposable as well.

Figure 2:
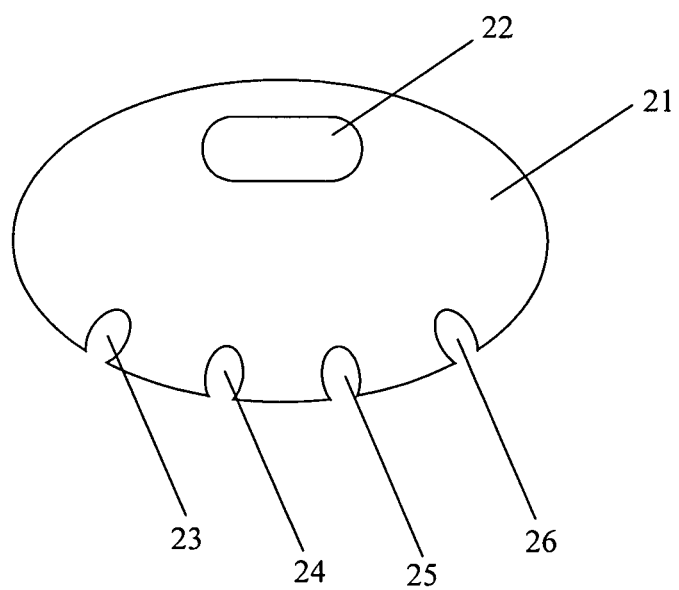
FIG. 2 illustrates another exemplary system for delivering drugs to a patient having a heating pad, according to some embodiments of the present invention.

FIG. 2 illustrates another exemplary embodiment of a heating pad, which is similar to the one discussed above with regard to FIG. 1. The heating pad of FIG. 2 includes a disposable part 21 and a reusable part 22. The embodiment of the heating pad of FIG. 2 is configured to perform injection using at least one of four "bays" 23-26 (or any other number or combination thereof) with the heating element disposed around each injection site. In some embodiments, the heating element can be configured to either partially or fully surround the respective injection site. In some embodiments, the heating can be applied to a larger portion of the heating site circumference. In some embodiments, the injection sites are provided in open areas (e.g., circles) which are fully embedded/within/inside the heating pad area similar to the circles 10-13 shown in FIG. 1.

Figure 5:
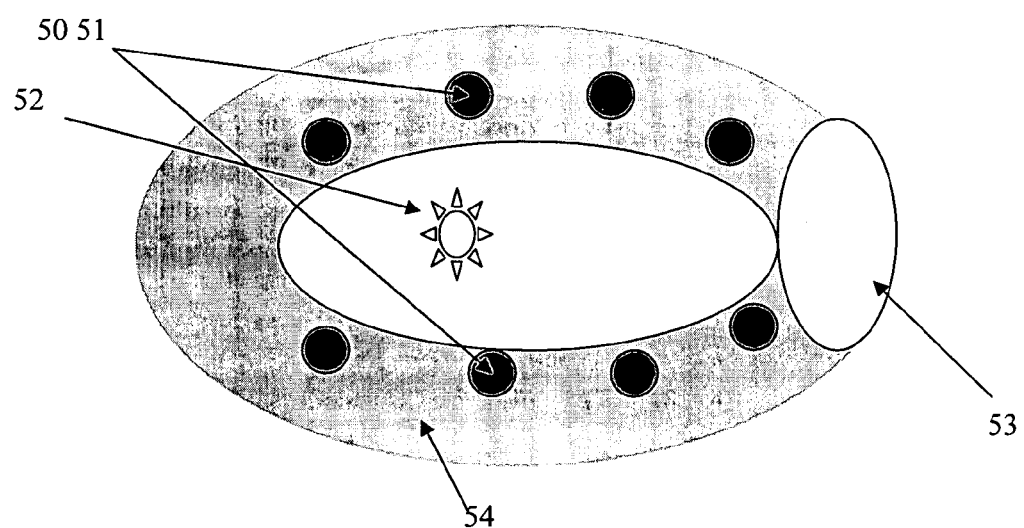
FIG. 5 illustrates another exemplary system for delivering drugs to a patient having a flexible heating pad, according to some embodiments of the present invention.

FIG. 5 illustrates another exemplary embodiment of the present invention, in which the injection sites are fully embedded within a flexible heating pad 54 area. The flexible heating pad 54 is configured to be connected to a reusable control unit 53. Reference numerals 50 and 51 together indicate the location of an injection site 52. Before injection, the patient may fold the skin between a thumb and an index finger of one hand located between reference numerals 50 and 51, respectively, and perform injection procedure between the two fingers at the injection site 52.

In some embodiments, the disposable part may include identification and/or counting means and/or tracking means, such that the reusable unit can identify whether the disposable part was already used or how many times the disposable part has been used for heating the injection site. Additionally, such means can limit the number of times that the heating pad is used and prevent it from being used more than a preset number of times that the heating pad is capable of heating. It can have include an indication means to indicate that the heating pad can no longer be used for heating and/or an indication of the number of times that the heating pad can be operated.

Such tracking means may include:
- a serial number, such as an EPROM chip, with a unique number that identifies the disposable part;
- an RFID chip that uniquely identifies the disposable part;
- an optical barcode that uniquely identifies disposable part;
- a mechanical attachment in the reusable part for attachment to the disposable part that can be used only once (such that it breaks when they are disconnected, for example); and
- a battery in the reusable part having enough energy for a limited preset number of usages.

The above illustrate non-limiting examples for modifying an electronic element (which is not disposable) and limiting the number of times it can be used before it has to be replaced. As can be understood by one skilled in the art, other ways to limit usage can be implemented.

Figure 6:
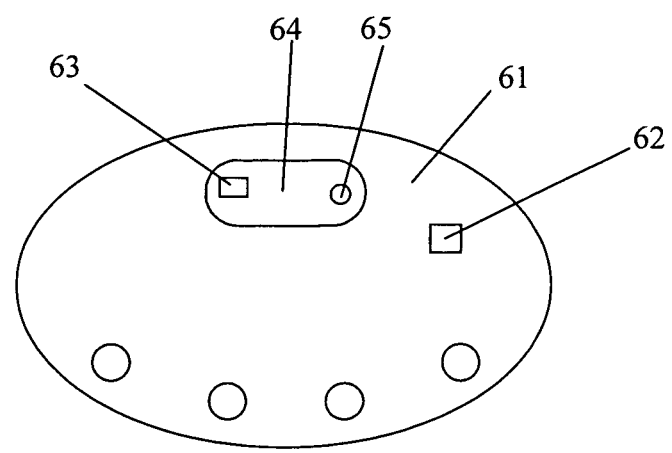
FIG. 6 illustrates another exemplary system for delivering drugs to a patient having a flexible heating pad, according to some embodiments of the present invention.

An example for such identification mechanism is schematically shown in FIG. 6. In the shown embodiment, the disposable element 61 includes a RFID chip 62 with a unique identification code, which can be read by an RFID reader 63, embedded in the reusable unit 64. The reusable unit 64 can identify the disposable element 61 once they are connected using a unique code written inside the RFID chip 62. The reusable unit stores this information inside a memory element, such as a non-volatile memory element. Each time the disposable element is used the information is written as well in the memory element. This way the reusable treatment element can count how many times the disposable part has been used for heating the injection site. Using that information, it can limit the number of times that the heating pad is used and prevent it from being used more than a preset number of times that the heating pad is capable of heating. The reusable unit 64 can include an indication means to indicate that the heating pad can no longer be used for heating, such as a red LED indicator 65 and/or an indication of the number of times that the heating pad can be operated, such as LED bar or numeric display (not shown).

In some embodiments, the disposable part includes a set of fuse-type conductive elements which can be manufactured together with the heating element using the same process, such as by conductive printing, PCB etching, or other known, and/or low cost manufacturing methods. The fuse-type conductive element can be produced by printing a short very narrow conductive element. For each use, the reusable part burns one fuse element by applying a short high electrical current signal to that element. Thus, the reusable unit can determine whether all fuse elements have been burned out and thus, whether the disposable part can be used again. These mechanisms provide an additional safety protection such that the disposable part will not be used beyond a predetermined number of injections and may be damaged, or influence the heating accuracy or the contact to the tissue.

In some embodiments, different numbers of injections are supported by the heating pad, such as a single use for a single injection or all the injections of few days, such as 3 days. In some embodiments, the reusable part has a real time clock that provides time and date and limits the use of each disposable unit for a given period, such as 1 day of use, without limiting the number of injections or treatment given at that period.

In some embodiments, the reusable part of the heating pad includes a timer or is in wireless communication with a timer that is used to remind the user of the timing for the next injection. Each time the injection is used, the timer is reset. This feature can provide the user with a reminder to perform an injection and prevent the user from repeated injections.

In some embodiments, the reusable and disposable parts can include means for detecting a volume of the injected subcutaneous drug stored in a depot and adjusting the tissue treatment (e.g., an amount of the drug being injected) according to that measurement. This can be achieved, for example, by adding an electrode to the disposable part which can be used for electrical impedance measurement and having in the reusable part electronics and a controller to support the impedance measurement. Once the drug is infused to the subcutaneous tissue, it alters the impedance measurement result and as it clears from the depot the impedance measurement returns to the baseline. Thus, by tracking the impedance measurement, the device can detect the clearance of the drug from the subcutaneous depot and the treatment to the tissue can be adjusted accordingly. For example, the treatment can depend on the volume of the drug depot as well as on the velocity by which the drug clears from the depot so that when the depot is cleared the treatment stops or if the clearance velocity is low the treatment can be increased.

Thus, it is seen that devices, systems and methods for improving the effectiveness of drug delivery upon injection are provided. Although particular embodiments have been disclosed herein in detail, this has been done by way of example for purposes of illustration only, and is not intended to be limiting with respect to the scope of the appended claims, which follow. In particular, it is contemplated by the applicant that various substitutions, alterations, and modifications may be made without departing from the spirit and scope of invention as defined by the claims. Other aspects, advantages, and modifications are considered to be within the scope of the following exemplary claims. The claims presented are representative of at least some of the inventions disclosed herein. Other, unclaimed inventions are also contemplated. Applicants reserve the right to pursue such inventions in later claims.

What is claimed is:

1. A treatment device, comprising:
   a treatment element having a plurality of injection sites for administering at least one injection of a drug into a tissue, wherein each injection site in the plurality of injection sites corresponds to a predetermined location on the tissue for injection of the drug at a specific time;
   a processor provided within the treatment element;
   a heating element provided within or adjacent to the treatment element, the heating element being controlled by and electrically coupled to the processor and configured to apply heat to the tissue at the predetermined location during at least one of before, during and after injection of the drug for a predetermined period of time such that the tissue is heated to a predetermined temperature which is less than a predetermined limiting temperature; and
   a temperature sensor electrically coupled to the processor and configured to provide a signal corresponding to the temperature of the tissue heated by the treatment element,
   wherein:
      based on the temperature of the tissue, the processor is configured to stabilize heating of the tissue to the predetermined temperature,
      application of heat by the heating element is configured to improve pharmacokinetic and/or pharmacodynamic properties of the drug, and
      the treatment element includes a disposable part and a reusable part, and
      the disposable part includes at least one identification element configured to determine whether the disposable part has been used.

2. The device according to claim 1, wherein the reusable part includes
   the processor;
   an energy source coupled to the processor and configured to provide energy to the device for applying heat at least once; and
   the temperature sensor.

3. The device according to claim 2, wherein the temperature sensor is configured to be in temperature communication with at least one of the following: the heated tissue surrounding the predetermined location and the heating element.

4. The device according to claim 1, wherein the at least one identification element include at least one of the following: an electrically-burnable element, serial number such as EPROM chip, an RFID chip, an optical barcode, and a mechanical attachment that can be used only once.

5. The device according claim 1, wherein the treatment element includes at least one injection site marker configured to indicate at least one injection site in the plurality of injection sites.

6. The device according to claim 1, wherein the treatment element includes an identification mechanism configured to identify a time when the drug is injected;
   wherein, based on information provided by the identification mechanism, the heating element is configured to automatically apply the heat.

7. The device according to claim 1, wherein the treatment element includes an identification mechanism configured to identify the predetermined injection location on the tissue;
   wherein, based on information provided by the identification mechanism, the heating element is configured to apply a predetermined heat profile.

8. The device according to claim 7, wherein the predetermined injection location corresponds to at least one meal type or at least one drug dose.

9. The device according to claim 1, wherein the treatment element includes an indicator configured to indicate that a specific injection site was used.

10. The device of according to claim 1, wherein the heating element is configured to be disposed in at least one of the following ways: adjacent to the predetermined location on the tissue, partially surrounding the predetermined location on the tissue, and completely surrounding the predetermined location on the tissue.

11. The device according to claim 1, wherein the treatment element includes a sensor configured to
   detect injection of the drug into the tissue; and,
   based on the detection, generate a signal to the processor to activate the heating element.

12. The device according to claim 6, wherein the identification mechanism includes at least one of the following: a sensor configured to sense folding of a skin, a pressure sensor disposed on the heating element, a pressure sensor disposed on a marker configured to mark a spot for placement of a finger during injection, and a proximity sensor configured to sense proximity of a device for injecting drug into the tissue.

13. The device according to claim 12, wherein the device for injecting drug into the tissue includes at least one of the following: a syringe and an injector pen.

14. The device according to claim 1, wherein the injected drug is insulin.

15. The device according to claim 1, wherein the treatment device includes at least one predetermined treatment profile dependent on a dosage and a type of the drug being injected.

16. The device according to claim 15, wherein the treatment device includes a mechanism configured to measure a volume of the injected drug stored in a tissue depot and further configured to adjust application of the heat based on the measured volume.

17. The device according to claim 16, wherein the measurement of the volume is performed using an electrical impedance measurement.

18. The device according to claim 1, wherein the treatment device includes a mechanism configured to generate an alert corresponding to a time of a next injection.

19. A method for administering a drug into a tissue comprising:
    providing a treatment device comprising:
        a treatment element having a plurality of injection sites for administering at least one injection of a drug into a tissue, wherein each injection site in the plurality of injection sites corresponds to a predetermined location on the tissue for injection of the drug at a specific time;
        a processor provided within the treatment element;
        a heating element provided within or adjacent to the treatment element, the heating element being controlled by and electrically coupled to the processor and configured to apply heat to the tissue at the predetermined location during at least one of before, during and after injection of the drug for a predetermined period of time such that the tissue is heated to a predetermined temperature which is less than a predetermined limiting temperature;
        a temperature sensor electrically coupled to the processor and configured to provide a signal corresponding to the temperature of the tissue heated by the treatment element;
        the treatment element includes a disposable part and a reusable part, and
        the disposable part includes at least one identification element configured to determine whether the disposable part has been used;
    placing the treatment element in temperature communicative contact with tissue at the predetermined location;
    administering the drug to the tissue at the predetermined location using a first injection site;
    applying the heat to the tissue at the predetermined location;
    determining a temperature of the tissue at the predetermined location; and
    controlling, based on the determined temperature, the heating of the tissue at the predetermined location to prevent heating the injected drug above the predetermined limiting temperature.

20. The method according to claim 19, wherein the applying further comprises
    determining a time when the drug is injected into the tissue; and
    applying, based on the determining, the heat.

21. The method according to claim 19, wherein the applying further comprises
    determining the predetermined location on the tissue; and
    applying, based on the determining, the heat.

22. The method of according to claim 19, wherein the applying further comprises
    applying the heat in at least one of the following ways: adjacent to the predetermined location on the tissue, partially surrounding the predetermined location on the tissue, and completely surrounding the predetermined location on the tissue.

23. The method according to claim 19, wherein the administering further comprises
    administering the drug using a device for injecting the drug into the tissue;
    wherein the device for injecting the drug includes at least one of the following: a syringe and an injector pen.

24. The method according to claim 19, wherein the administered drug is insulin.

* * * * *